US009248608B2

(12) United States Patent
Ogasawara et al.

(10) Patent No.: US 9,248,608 B2
(45) Date of Patent: Feb. 2, 2016

(54) MANUFACTURING METHOD AND MANUFACTURING APPARATUS OF AN ABSORBENT BODY

(75) Inventors: Yoshikazu Ogasawara, Kagawa (JP); Takanori Yano, Kagawa (JP); Masahiko Ishikawa, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 161 days.

(21) Appl. No.: 13/501,336

(22) PCT Filed: Oct. 8, 2010

(86) PCT No.: PCT/JP2010/067736
§ 371 (c)(1),
(2), (4) Date: Jun. 14, 2012

(87) PCT Pub. No.: WO2011/048964
PCT Pub. Date: Apr. 28, 2011

(65) Prior Publication Data
US 2012/0312463 A1    Dec. 13, 2012

(30) Foreign Application Priority Data
Oct. 19, 2009    (JP) .................................. 2009-240707

(51) Int. Cl.
*B29C 65/00*    (2006.01)
*B29C 65/70*    (2006.01)
(Continued)

(52) U.S. Cl.
CPC ........... *B29C 65/70* (2013.01); *A61F 13/15585* (2013.01); *A61F 13/15634* (2013.01);
(Continued)

(58) Field of Classification Search
CPC .............. A61F 13/15658; A61F 13/15; A61F 13/15577; A61F 13/15617; A61F 13/15634; A61F 13/53; A61F 13/15585; B29C 65/70; B29C 39/00; B29C 63/00
USPC ........................................................ 156/245
See application file for complete search history.

(56) References Cited

U.S. PATENT DOCUMENTS 4,119,450 A    10/1978    Bianco
4,598,441 A *  7/1986    Stemmler ....................... 19/145
(Continued)

FOREIGN PATENT DOCUMENTS

CN    1988863 A    6/2007
EP    1427658 B1   6/2006
(Continued)

OTHER PUBLICATIONS
International Search Report for PCT/JP2010/067736 dated Nov. 16, 2010.
(Continued)

*Primary Examiner* — Philip Tucker
*Assistant Examiner* — Vicki Wu
(74) *Attorney, Agent, or Firm* — Hauptman Ham, LLP

(57) ABSTRACT

A manufacturing method of an absorbent body used for an absorbent article, includes molding the absorbent body by sucking in a gas, mixed with a liquid absorbent fiber and a superabsorbent polymer, using a suction hole at a bottom portion of a mold, and laminating the liquid absorbent fiber and the superabsorbent polymer on the bottom portion, and making a lamination thickness of the absorbent body thin by sucking out gas in the absorbent body placed on a placement surface on which the absorbent body is placed by, after the molding, in a state in which the gas is not supplied, sucking air through the suction hole on the placement surface, and creating an air pressure, in a space in between fibers in the absorbent body while sucking out the air, lower than that in a space in between fibers in the absorbent body while laminating in molding.

4 Claims, 10 Drawing Sheets

(51) Int. Cl.
*A61F 13/53* (2006.01)
*B29C 63/00* (2006.01)
*B29C 39/00* (2006.01)
*A61F 13/15* (2006.01)

(52) U.S. Cl.
CPC .......... *A61F13/15658* (2013.01); *A61F 13/53* (2013.01); *B29C 39/00* (2013.01); *B29C 63/00* (2013.01); *A61F 13/15* (2013.01); *A61F 13/15577* (2013.01); *A61F 13/15617* (2013.01)

(56) References Cited

U.S. PATENT DOCUMENTS

| | | | |
|---|---|---|---|
| 6,330,735 B1 * | 12/2001 | Hahn et al. | 19/296 |
| 2001/0006089 A1 * | 7/2001 | Ando et al. | 156/206 |
| 2004/0061263 A1 * | 4/2004 | Daniels et al. | 264/518 |
| 2006/0021695 A1 * | 2/2006 | Blessing et al. | 156/196 |
| 2006/0048880 A1 * | 3/2006 | Blessing et al. | 156/60 |
| 2006/0105075 A1 | 5/2006 | Otsubo | |
| 2011/0072582 A1 * | 3/2011 | Patterson et al. | 5/484 |

FOREIGN PATENT DOCUMENTS

| | | | |
|---|---|---|---|
| JP | 51135738 A | 11/1976 | |
| JP | 63139547 A | 6/1988 | |
| JP | 7119013 A | 5/1995 | |
| JP | 10137286 A | 5/1998 | |
| JP | 2001171029 A | 6/2001 | |
| JP | 2005513288 A | 5/2005 | |
| JP | 2006141615 A | 6/2006 | |
| JP | 2007167509 A | 7/2007 | |
| JP | 2008508036 A | 3/2008 | |
| JP | 2008508052 A | 3/2008 | |
| JP | 2008132055 A | 6/2008 | |
| JP | 2008154774 A | 7/2008 | |
| JP | 2008206539 A | 9/2008 | |
| JP | 2008-231609 A | 10/2008 | |
| JP | 2009219710 A | 10/2009 | |
| WO | 2006014854 A1 | 2/2006 | |

OTHER PUBLICATIONS

Office Action mailed Jul. 16, 2013 corresponds to Japanese patent application No. 2009-240707.

Office Action mailed Aug. 15, 2013 corresponds to Chinese patent application No. 201080047082.5.

European Search Report dated Feb. 13, 2013.

Office Action issued Aug. 27, 2014, corresponding to U.S. Appl. No. 13/687,431.

* cited by examiner

MANUFACTURING METHOD AND MANUFACTURING APPARATUS OF AN ABSORBENT BODY

RELATED APPLICATIONS

The present application is a National Phase of International Application Number PCT/JP2010/067736, filed Oct. 8, 2010, and claims priority from, Japanese Application Number 2009-240707, filed Oct. 19, 2009.

TECHNICAL FIELD

The present invention relates to a manufacturing method and a manufacturing apparatus of an absorbent body used for an absorbent article such as a disposable diaper.

BACKGROUND ART

A disposable diaper and a sanitary napkin are known as absorbent articles that absorb liquid such as bodily waste fluid. Such an absorbent article includes as a component part an absorbent body that absorbs a liquid, and this absorbent body is formed by molding into a predetermined shape a liquid absorbent fiber such as pulp fiber made by mixing therein superabsorbent polymer (a high molecular weight polymer having a high liquid holding ability and that swells and the like by absorbing liquid).

On the other hand, with a view to providing a better appearance when clothes are worn and decreasing the sense of bulkiness, there is a need to make thinner an absorbent article such as the diaper and the sanitary napkin.

In regards to this point, PTL 1 discloses, in a method that makes an absorbent body thin, passing through and sandwiching and pressing an absorbent body in between a pair of rollers which are opposed to each other and rotate.

CITATION LIST

Patent Literature

PTL 1: Japanese Translation of PCT International Application No. 2005-513288

SUMMARY OF INVENTION

Technical Problem

The method in PTL 1, however, is for a pair of rollers to contact and physically squash the absorbent body. Thus, in accordance with this, the granular superabsorbent polymer in the absorbent body will also be squashed and harden. Then, there is a possibility that the absorbent body as a whole will become firm, and as a result will give the wearer a sense of discomfort when wearing the absorbent article.

Further, in the case where a distribution density of the superabsorbent polymer in the absorbent body is varied, in a region with high distribution density, due to the sandwiching and pressing of the above absorbent body a large number of superabsorbent polymers also get excessively squashed and harden, and therefore the hardness of this region becomes higher than that of other regions in the absorbent body. In other words, inconsistency of hardness is made apparent or is enlarged, and thus this also becomes the reason for the sense of discomfort when wearing as described above.

Further, in an area where a large number of superabsorbent polymers are squashed, such polymers connect flatly and spread and the like in a surface that intersects the thickness direction of the absorbent body, and gel blocking easily happens (a phenomenon where the superabsorbent polymer that has absorbed liquid swells and connects as a wall, and this wall inhibits the liquid from permeating in the thickness direction), in other words there is also a possibility that inhibition of liquid absorption occurs.

An advantage of some aspects of the present invention is to provide a manufacturing method of an absorbent body, which can be made thin in thickness, by suppressing squashing of a superabsorbent polymer, and a manufacturing apparatus thereof.

Solution to Problem

An aspect of the invention is a manufacturing method of an absorbent body used for an absorbent article, the method comprising:
  molding the absorbent body by sucking in gas, mixed with a liquid absorbent fiber and a superabsorbent polymer, using a suction hole at a bottom portion of a mold, and laminating the liquid absorbent fiber and the superabsorbent polymer on the bottom portion; and
  making a lamination thickness of the absorbent body thin by sucking out gas in the absorbent body placed on a placement surface on which the absorbent body is placed by,
    after the molding, in a state in which the gas is not supplied, sucking air through the suction hole on the placement surface, and creating an air pressure, in a space in between fibers in the absorbent body while sucking out the air, that is lower than an air pressure in a space in between fibers in the absorbent body while laminating in the molding.

Another aspect of the invention is a manufacturing apparatus of an absorbent body used for an absorbent article, the apparatus comprising:
  a first apparatus that molds the absorbent body by sucking in a gas, mixed with a liquid absorbent fiber and a superabsorbent polymer, using a suction hole at a bottom portion of the mold, and laminating the liquid absorbent fiber and the superabsorbent polymer on the bottom portion; and
  a second apparatus that makes a lamination thickness of the absorbent body thin by sucking out gas in the absorbent body placed on a placement surface on which the absorbent body is placed by,
    in a state in which the gas is not supplied, sucking the air through the suction hole on the placement surface, and creating an air pressure, in a space in between fibers in the absorbent body while sucking out the air, that is lower than an air pressure in a space in between fibers in the absorbent body while laminating in the molding.

Other features of this invention will become clear from the present specification and the description of the attached drawings.

Advantageous Effects of Invention

According to this invention, an absorbent body can be made thin in thickness, by suppressing squashing of a superabsorbent polymer.

DESCRIPTION OF EMBODIMENTS

Figure 1:
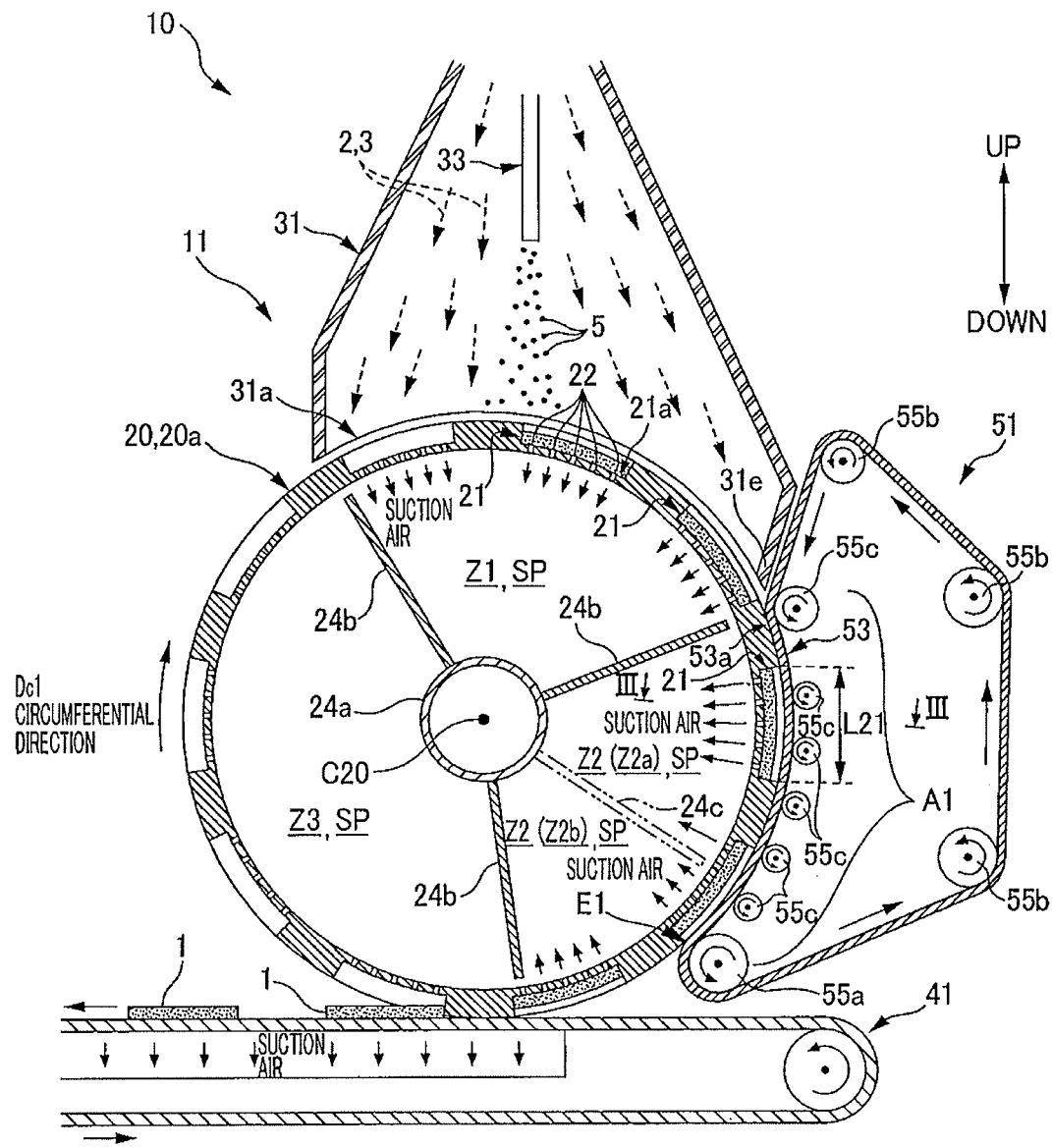
FIG. 1 is a central vertical cross sectional view of an example of a manufacturing apparatus 10 used in a manufacturing method of an absorbent body 1 according to a first embodiment.

At least the following matters will become clear through the description of the present specification and the accompanying drawings.

A manufacturing method of an absorbent body used for an absorbent article, the method comprising:

molding the absorbent body by sucking in a gas, mixed with a liquid absorbent fiber and a superabsorbent polymer, using a suction hole at a bottom portion of a mold, and laminating the liquid absorbent fiber and the superabsorbent polymer on the bottom portion; and making a lamination thickness of the absorbent body thin by sucking out gas in the absorbent body placed on a placement surface on which the absorbent body is placed by, after the molding, in a state in which the gas is not supplied, sucking air through the suction hole on the placement surface, and creating an air pressure, in a space in between fibers in the absorbent body while sucking out the air, that is lower than an air pressure in a space in between fibers in the absorbent body while laminating in the molding.

According to this manufacturing method of an absorbent body, after the laminating of the absorbent body, the air in spaces in between fibers is sucked up by sucking the air through the suction holes, and making an air pressure in a space in between fibers in the absorbent body lower than an air pressure in a space in between fibers in the absorbent body while laminating. Thus, the fibers are moved so that there is no space, that is the fibers are moved to be closely packed, and the lamination thickness of the absorbent body is made thin. Therefore, while suppressing squashing of the superabsorbent polymers, the thickness of the absorbent body can be made thin.

A manufacturing method of an absorbent body used for an absorbent article, wherein preferably in making the lamination thickness thin, a covering member is arranged that opposes the placement surface and that covers the absorbent body from a side opposite the placement surface, and inflow of outside air into the absorbent body is suppressed by the placement surface and the covering member.

According to such a manufacturing method of the absorbent body, inflow of outside air into the absorbent body while sucking air to suck up the air in the spaces in between fibers is suppressed by the covering member. Thus, the air pressure of the space in between fibers in the absorbent body while sucking out the air can be more easily lowered.

Further, the suction air amount of the suction of air can be made small, and the power needed for this suction of air can be made small. As a result, energy costs in manufacturing can be saved.

A manufacturing method of an absorbent body used for an absorbent article, wherein preferably the covering member is arranged in a non-contacting manner with the absorbent body.

According to such a manufacturing method of the absorbent body, physically sandwiching and pressing the absorbent body with both the placement surface and the covering member is prevented, and as a result squashing of the superabsorbent polymers can be more effectively suppressed.

A manufacturing method of an absorbent body used for an absorbent article, wherein preferably the absorbent body is transported by the placement surface which is moving along a predetermined travel path, the covering member is a belt member, and at least while making the lamination thickness thin, the belt member moves along the travel path together with the moving placement surface.

According to such a manufacturing method of the absorbent body, at least while making the lamination thickness thin, the belt member that is a covering member moves along the travel path together with the moving placement surface. Therefore, any slip between the absorbent body, that is being transported substantially integrally with the holding surface, and the belt member can be suppressed, and thus peeling off of the absorbent body from the placement surface can be effectively prevented. As a result, the absorbent body can be stably manufactured.

A manufacturing method of an absorbent body used for an absorbent article, wherein preferably the placement surface is a portion of a predetermined surface included in a predetermined member, the predetermined surface has a width direction intersecting a direction along the travel path, and the belt member closely contacts a portion of an outer side in the width direction of the placement surface of the predetermined surface, in a range in which the belt member moves along the travel path together with the moving placement surface.

According to this manufacturing method of the absorbent body, the belt member closely contacts the portion of the outer side in the width direction of the placement surface of the absorbent body. Therefore, airtightness of an accommodating space of the absorbent body that is defined by the belt member and the placement surface can be increased. As a result, the air pressure in the space in between the fibers in the absorbent body can be effectively decreased.

A manufacturing method of an absorbent body used for an absorbent article, wherein preferably in the molding, the absorbent body is molded by having the mold formed in a concave shape on an outer circumferential face, and by using a first rotating drum that continuously rotates in one direction in a circumferential direction, a supply duct provided in a predetermined position in the circumferential direction and that supplies a gas, with the liquid absorbent fiber and the superabsorbent polymer mixed therein, towards the outer circumferential face, and a mold-release mechanism that releases the absorbent body from the mold and that is provided on a downstream side of the predetermined position in the circumferential direction, the placement surface in accordance with making the lamination thickness thin is the bottom section of the mold, and the covering member is arranged opposite the outer circumferential face, in a position between the supply duct and the mold-release mechanism in the circumferential direction of the first rotating drum.

According to this manufacturing method of the absorbent body, the covering member is arranged opposed to the outer circumferential face of the first rotating drum, and the process to make the lamination thickness of the absorbent body thin is performed with the first rotating drum. Therefore, it is not necessary to provide other rotating drums and the like, and simplification and space saving of the apparatus configuration can be realized.

A manufacturing method of an absorbent body used for an absorbent article, wherein preferably in the molding, the absorbent body is molded by having the mold formed in a concave shape on an outer circumferential face, and by using a first rotating drum that continuously rotates in one direction in a circumferential direction, and a supply duct provided in a predetermined position in the circumferential direction and that supplies a gas, with the liquid absorbent fiber and the superabsorbent polymer mixed therein, towards the outer circumferential face, and in making the lamination thickness thin, includes a second rotating drum provided on a downstream side of the predetermined position in the circumferential direction, and that receives the absorbent body from the mold of the first rotating drum, the placement surface, in accordance with making the lamination thickness thin, is a portion of an outer circumferential face of the second rotating drum, and the second rotating drum rotates in one direction in a circumferential direction, while the placement surface holds the absorbent body received from the first rotating drum on the outer circumferential face, using air sucked through a suction hole on the holding surface, and the covering member is arranged in a predetermined position in the circumferential direction, while opposing the outer circumferential face of the second rotating drum.

According to this manufacturing method of the absorbent body, the second rotating drum can be used as an apparatus dedicated to making the lamination thickness of the absorbent body thin. Therefore, the specification of the hole diameter of the suction hole and its arrangement pattern and the like on the outer circumferential face of the second rotating drum can be designed as a specification specialized in making the lamination thickness thin. As a result, making the lamination thickness thin, while suppressing squashing of the superabsorbent polymers, can be more surely performed.

A manufacturing method of an absorbent body used for an absorbent article, wherein preferably the outer circumferential face of the second rotating drum is formed into a substantially smooth surface, without a recessed portion that has a depth deeper than a lamination thickness of the absorbent body when receiving the absorbent body from the first rotating drum, the covering member is a belt member opposing the circumferential face of the second rotating drum and arranged in a predetermined position in the circumferential direction, and the belt member moves along the outer circumferential face together with the moving placement surface, at least while making the lamination thickness thin, and the belt member is sucked toward the outer circumferential face using the air sucked through the suction hole, and sandwiches and presses the absorbent body, together with the placement surface, on the outer circumferential face.

According to this manufacturing method of the absorbent body, the outer circumferential face of the second rotating drum is formed as a substantially smooth surface, the substantially smooth surface not having a concave portion that is deeper than a lamination thickness of the absorbent body. Therefore, in addition to making the lamination thickness thin by sucking up the air from the spaces in between fibers in the absorbent body, the absorbent body can be sandwiched and pressed by the belt member and the placement surface of the outer circumferential face. As a result, the lamination thickness of the absorbent body can be made much thinner.

A manufacturing method of an absorbent body used for an absorbent article, wherein preferably the placement surface is formed on one side of a moving member that moves along a predetermined travel path, and on a surface opposite to the placement surface of the moving member is positioned opposed a space which enables the sucking of the air through the suction hole on the placement surface, the space is defined into a plurality of zones along the travel path, and a covering member is arranged that opposes the placement surface and covers the side of the absorbent body opposite to the placement surface, in a predetermined range of the travel path, an air pressure of a zone corresponding to the predetermined range of the plurality of zones is lower than that of a zone corresponding to a position on a downstream side of the predetermined range, and an air pressure of a zone corresponding to a downstream end in the predetermined range is set to a value between an air pressure of a zone other than a zone corresponding to the downstream end of the zones corresponding to the predetermined range and an air pressure of a zone corresponding to a position on a downstream side of the predetermined range.

According to this manufacturing method of the absorbent body, the zone corresponding to the downstream end functions as a buffer zone when changing air pressure. In other words, a rapid suction air pressure fluctuation which may occur when the placement surface changes from a low air pressure zone (a zone other than a zone corresponding to the downstream end of the zones corresponding to the predetermined range) to a high air pressure zone (a zone corresponding to a position on a downstream side of a predetermined range) can be relieved, and falling off or peeling off of the absorbent body from the placement surface and the like due to the suction air pressure fluctuation can be effectively prevented.

Further, a manufacturing apparatus of an absorbent body used for an absorbent article, the apparatus comprising:

a first apparatus that molds the absorbent body by sucking in a gas, mixed with a liquid absorbent fiber and a superabsorbent polymer, using a suction hole at a bottom portion of the mold, and laminating the liquid absorbent fiber and the superabsorbent polymer on the bottom portion; and a second apparatus that makes a lamination thickness of the absorbent body thin by sucking out gas in the absorbent body placed on a placement surface on which the absorbent body is placed by, in a state in which the gas is not supplied, sucking the air through the suction hole on the placement surface, and creating an air pressure, in a space in between fibers in the absorbent body while sucking out the air, that is lower than an air pressure in a space in between fibers in the absorbent body while laminating in the molding.

According to this manufacturing apparatus of the absorbent body, a similar effect as the above-described manufacturing method can be realized.

First Embodiment

Figure 2A:
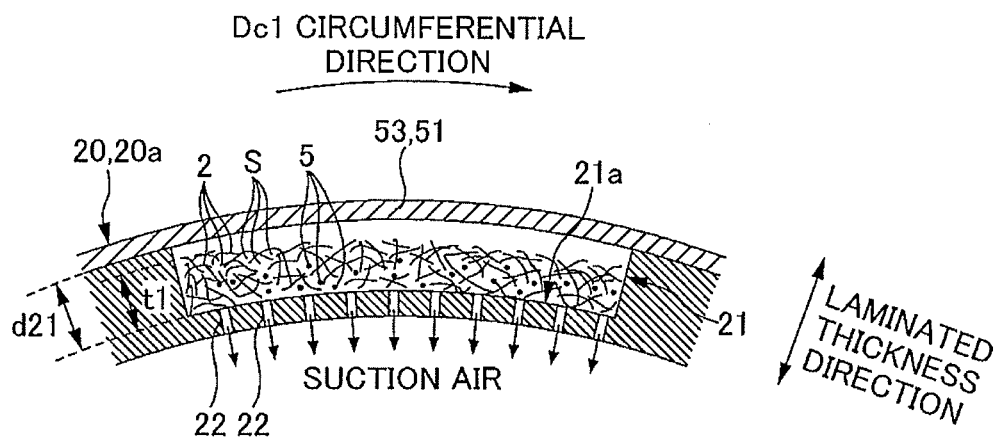
FIG. 2A and FIG. 2B are explanatory views of a thinning process of the absorbent body 1.
Figure 2B:
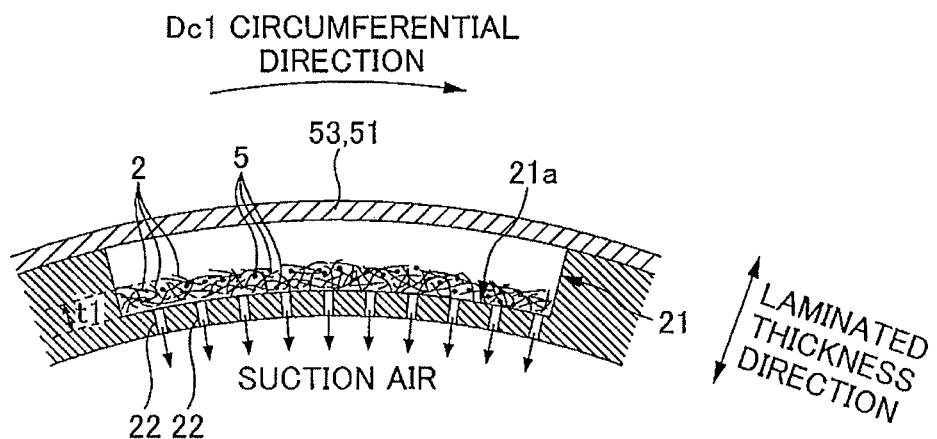
Figure 3:
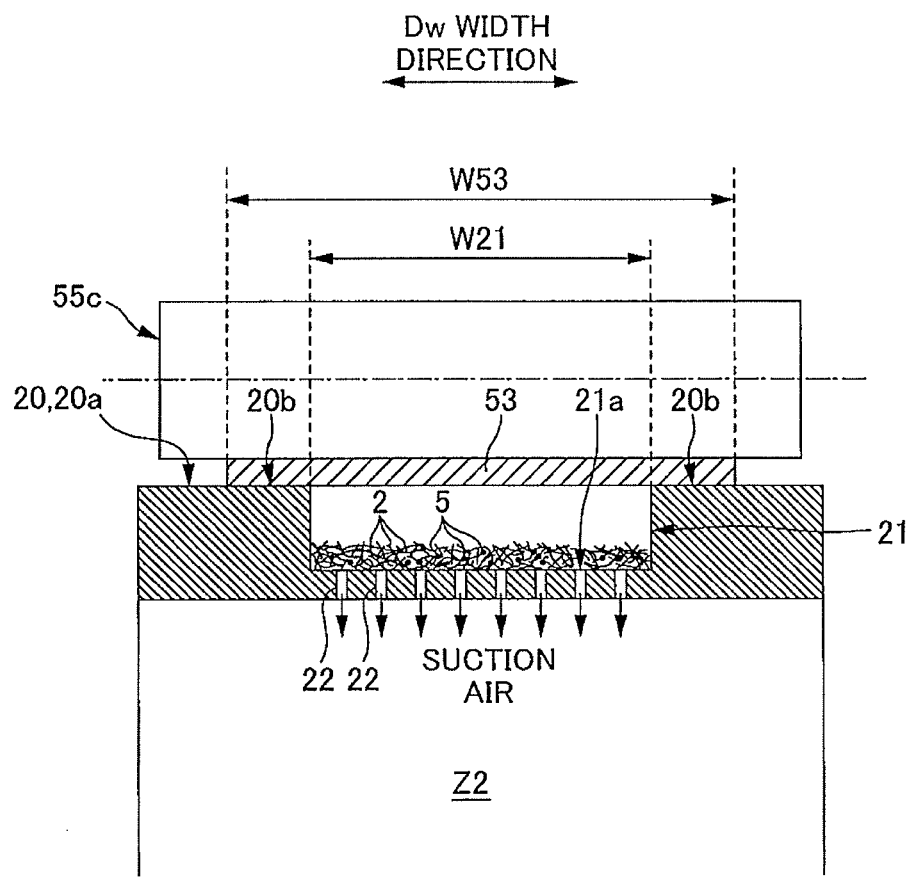
FIG. 3 is an III-III cross sectional view of FIG. 1.

FIG. 1 is a central vertical cross sectional view of an example of a manufacturing apparatus 10 used in a manufacturing method of an absorbent body 1 according to a first embodiment. FIG. 2A and FIG. 2B are explanatory views of a thinning process of the absorbent body 1, and FIG. 2A shows a state before processing or a first half of the processing, and FIG. 2B shows a state in a second half or after processing. Further, FIG. 3 is an III-III cross sectional view of FIG. 1.

A manufacturing method of the absorbent body 1 according to a first embodiment is a manufacturing method of a thin absorbent body 1. In other words, the manufacturing method of the absorbent body 1 includes an absorbent body molding process that molds the absorbent body 1 by laminating pulp fiber 2 (corresponding to liquid absorbent fiber) including superabsorbent polymer 5, and an absorbent body thinning process that makes a lamination thickness of the molded absorbent body 1 thin while substantially maintaining a basis weight.

The former absorbent body molding process is performed by a so-called fiber stacking apparatus 11, and further, in regards to the latter absorbent body thinning process, a thinning apparatus 51 arranged near the fiber stacking apparatus 11 is to perform the process in association with the fiber stacking apparatus 11. In other words, the fiber stacking apparatus 11 corresponds to a "first apparatus" and a "second apparatus", and the thinning apparatus 51 corresponds to the "second apparatus". Hereinbelow, the fiber stacking apparatus 11 and the thinning apparatus 51 are described.

<<<Fiber Stacking Apparatus 11>>>

The fiber stacking apparatus 11 includes, for example, (1) a rotating drum 20 that drivingly rotates continuously in one direction of a circumferential direction Dc1 (for example, clockwise) with a horizontal shaft C20 as a rotational center, (2) a supply duct 31 that discharges and supplies mixed air 3 (corresponding to a gas), including pulp fiber 2, towards an outer circumferential face 20a of the rotating drum 20 from a supply opening 31a arranged in a predetermined position in the circumferential direction Dc1 of the rotating drum 20, (3) a polymer inserting duct 33 included in the supply duct 31 and that discharges the granular superabsorbent polymer 5 towards the outer circumferential face 20a, and (4) a suction conveyor 41 (corresponding to a mold-release mechanism) arranged on a downstream side in the circumferential direction Dc1 of the supply duct 31, and that sucks the absorbent body 1 in order to mold release it from a mold 21 on the outer circumferential face 20a of the rotating drum 20 and transports it.

Hereinbelow, the circumferential direction Dc1 of the rotating drum 20 is merely referred to as the "circumferential direction Dc1", and a direction along the horizontal shaft C20 of the rotating drum 20 (a direction passing through a plane of paper in FIG. 1) is referred to as a "width direction Dw". Note that this width direction Dw is perpendicular to the circumferential direction Dc1.

The rotating drum 20 (corresponding to a moving member, and a first rotating drum) is a substantially cylindrical body, and on its outer circumferential face 20a is included, intermittently in a predetermined pitch in a circumferential direction Dc1, the molds 21 in a concave form corresponding to a form of the absorbent body 1 to be molded. Then, at a bottom section 21a of each mold 21 (corresponding to a placement surface) are provided a plurality of suction holes 22, and through these suction holes 22 an inner side of the mold 21 is in communication with an inner circumferential side of the rotating drum 20 in a permeable manner.

On the other hand, on the inner circumferential side of the rotating drum 20 is included a cylindrical division wall 24a concentrically with the rotating drum 20, and thus on the inner circumferential side of the rotating drum 20 is defined a doughnut shaped substantially closed space SP (corresponding to a space). Further, this substantially closed space SP is zone divided in the circumferential direction Dc1 by a plurality of division walls 24b, 24b, 24b. Therefore, for example, a first zone Z1 shown in FIG. 1 is maintained at a negative pressure state with an air pressure lower than the outside air pressure, and on the other hand, an air pressure P3 of a third zone Z3 on a further downstream side thereof is maintained at the same pressure as the outside air pressure or at an air pressure value in between the outside air pressure and an air pressure P1 of the first zone Z1. Then, in correspondence to this first zone Z1, a supply opening 31a of the supply duct 31 is arranged, and on the other hand, the suction conveyor 41 is arranged in correspondence to the third zone Z3. Note that, a second zone Z2 positioned in between these first and third zones Z1, Z3 is related to the absorbent body thinning process and this will be described later.

According to such fiber stacking apparatus 11, the absorbent body 1 is molded as follows. Firstly, by the driving rotation of the rotating drum 20, the mold 21 is moved along a path, along the outer circumferential face 20a, as a travel path. Then, when this mold 21 is passing the position of the supply duct 31, substantially only air of the mixed air 3 discharged and supplied from the supply opening 31a is sucked into the suction holes 22 on the bottom section 21a of the mold 21, and thus on the bottom section 21a are laminated the pulp fiber 2 and the superabsorbent polymer 5 in the mixed air 3 and the absorbent body 1 is manufactured. Then, when the mold 21 reaches a position opposing the suction conveyor 41, via a position of the thinning apparatus 51 to be described later, the absorbent body 1 in the mold 21 is sucked towards the outside by the suction air from the suction conveyor 41 and successively mold-released from the mold 21, and thereafter transported by the suction conveyor 41.

<<<Thinning Apparatus 51>>>

The thinning apparatus 51 is to make a lamination thickness of the absorbent body 1 thin, and this apparatus 51 is arranged in a position between the supply duct 31 and the suction conveyor 41 in the circumferential direction Dc1 of the rotating drum 20 and opposing the outer circumferential face 20a of the rotating drum 20.

According to this apparatus 51, in association with the rotating drum 20, the air pressure Pf2 in the space S in between the pulp fibers in the absorbent body 1 that has been laminated and molded in the mold 21 is made lower than the air pressure Pf1 in the space S in between the pulp fibers in the absorbent body 1 while laminating using the supply duct 31. In this way, the air in the space S in between the pulp fibers in the absorbent body 1 is sucked up to move the fibers 2 towards the bottom portion 21a so that the pulp fibers 2 become closely packed, from the state shown in FIG. 2A to the state shown in FIG. 2B, and the lamination thickness t1 of the absorbent body 1 is made thin. Here, in this thinning process, the space S in between the pulp fibers is only packed by the movement of the pulp fibers 2, and therefore the superabsorbent polymers 5 in the absorbent body 1 are generally not squashed, and their forms are maintained in a granular shape of the original form when injected into the mold 21. As a result, hardening and unevenness in hardness of the absorbent body 1 due to the thinning is effectively prevented.

Such thinning apparatus 51 has a non-air permeable endless belt 53 (corresponding to a belt member) that moves in a predetermined circular orbit as a main body, and this endless belt 53 has a portion of its circular orbit arranged along a portion of the outer circumferential face 20a of the rotating drum 20 in an arc shape. Therefore, in a range A1 along this arc shape (hereinbelow, referred to as a belt setting range A1), the endless belt 53 covers the absorbent body 1 on a side opposite side from the bottom section 21a of the mold 21 by its flat outer circumferential face 53a, and moves together with the movement of the mold 21 in the circumferential direction Dc1 at substantially the same speed as the mold 21.

Then, while the mold 21 is moving in this belt setting range A1, air in a space S in between the pulp fibers in the absorbent body 1 is sucked up by the suction air from the suction holes 22 on the bottom section 21a of this mold 21, and at this time, the endless belt 53 effectively suppresses the inflow of outside air into the absorbent body 1 with its non-air permeability. Therefore, an air pressure Pf2 in the space S in between the pulp fibers that defines the above air sucking ability is easily lowered, and as a result the lamination thickness t1 of the absorbent body 1 can be made thinner. Further, the air suction amount from the suction holes 22 to maintain the air pressure Pf2 in the space S in between the pulp fibers to the above level can be made small, and thus, the necessary power of a blower, for example, for the suction of air, can be made small.

By the way, suction of air of the suction holes 22 in this belt setting range A1 is performed based on an air pressure P2 of the second zone Z2 in the rotating drum 20. Then, a value of the air pressure P2 of the second zone Z2 is set as, for example, an air pressure value where an air pressure Pf2 of the space S in between the pulp fibers in the absorbent body 1 in a state where the mold 21 is covered by the endless belt 53 becomes lower than an air pressure Pf1 of the space S in between the pulp fibers in the absorbent body 1 at the time of lamination by the supply duct 31.

As an example, the air pressure P2 of the second zone Z2 is set as the same pressure or a lower pressure than the air pressure P1 of the first zone. The reason that it can be the same pressure is because while laminating in the first zone Z1, the mixed air 3 is supplied into the supply duct 31, but in the second zone Z2, the mixed air 3 is not supplied, and inflow of the outside air into the absorbent body 1 can be suppressed by the endless belt 53.

Note that, in some cases, the second zone Z2 may be further subdivided into a plurality of zones in the circumferential direction Dc1 by a division wall 24c. In the example in FIG. 1, it is subdivided into two zones Z2a, Z2b. Then, in the case of such subdivision, preferably, an air pressure P2b of a zone Z2b corresponding to a downstream end E1 in the circumferential direction Dc1 of the belt setting range A1 may be set to a value in between the air pressure P2a of the zone Z2a adjacent to the upstream side thereof and an air pressure P3 of the third zone Z3 adjacent to the downstream side thereof. Then, the zone Z2b corresponding to the downstream end E1 of the belt setting range A1 functions as a buffer zone in air pressure change, in other words, a sudden air pressure fluctuation that may occur when the mold 21 moves from the low air pressure second zone Z2 to the high air pressure third zone Z3 can be relieved, and dropping off or peeling off and the like of the absorbent body 1 from the mold 21 due to the suction air pressure fluctuation can be effectively prevented.

Here, preferably, from the view of inflow suppression of outside air into the absorbent body 1, preferably a width W53 of the endless belt 53 is made wider than a size W21 of the width direction Dw of the mold 21 as shown in FIG. 3. Then, the endless belt 53, that has been sucked towards the outer circumferential face 20a by the suction air from the suction holes 22 of the mold 21, adopts a closely contacting state for each portion 20b, 20b at an outer side in the width direction Dw of the mold 21 on the outer circumferential face 20a (corresponding to a predetermined surface) of the rotating drum 20 (corresponding to a predetermined member) as shown in FIG. 3. Therefore, inflow of the outside air from the width direction Dw is effectively prevented. Further, from a similar view, in addition to the above, preferably a length in the circumferential direction Dc1 of the belt setting range A1 shown in FIG. 1 is set longer than an entire length L21 of the circumferential direction Dc1 of the mold 21, and more preferably, set longer than 1.5 times of the entire length L21. Then, the mold 21 in which the air in the space S in between the pulp fibers is being sucked up can be covered up by the endless belt 53 from all directions (all directions of the width direction Dw and the circumferential direction Dc1) of its four peripheral edges, and therefore outside air inflow into the absorbent body 1 can be almost completely prevented.

Further, as can be understood by referring to FIG. 2A, a depth direction and a lamination thickness direction of the mold 21 are in the same direction. Therefore, preferably, a depth d21 of the bottom section 21a of the mold 21, with the outer circumferential face 20a of the rotating drum 20 as a reference, is set deeper than a target lamination thickness t1 of the absorbent body 1 while laminating by the supply duct 31. Then, in this process of the thinning apparatus 51, the endless belt 53 and the absorbent body 1 can be made to be in a substantially entirely non-contacting state. Therefore, sandwiching and pressing the absorbent body 1 physically with both the bottom portion 21a of the mold 21 and the endless belt 53 can be effectively avoided, and as a result squashing of the superabsorbent polymers can be further suppressed.

By the way, as shown in FIG. 1, a circular orbit of the endless belt 53 is formed by the endless belt 53 being put around a plurality of pass-line rollers 55a, 55b, 55c arranged in predetermined positions. Then, at least one of these pass-line rollers 55a, 55b, 55c is configured as a driving roller 55a connected to a driving source such as a motor. Therefore, by appropriately speed-controlling and the like the driving source, and drive-controlling the moving speed of the endless belt 53 in the belt setting range A1, with the moving speed of the mold 21 as a target speed, then the endless belt 53 and the mold 21 can be moved at substantially the same speed as each other as described above.

Here, preferably, of these pass-line rollers 55a, 55b, 55c, the rollers 55c, 55c ... that are in charge of an orbit of the belt setting range A1, in other words, the rollers 55c, 55c ... that are in charge of an arc shaped orbit along the outer circumferential face 20a of the rotating drum 20, are guided movably in a separating direction in respect to the outer circumferential face 20a of the rotating drum 20 by appropriate guide members, and a pressing force is added in a pressing direction to the outer circumferential face 20a by an elastic member such as a spring. Then, the endless belt 53 can be easily maintained in a surface contacting state to the outer circumferential face 20a of the rotating drum 20, and the airtightness in the mold 21 is increased (refer to FIG. 3). Further, a tension of the endless belt 53 can be easily maintained at a certain value, so that a running state of the endless belt 53 can also be stabilized.

Further, from the view of suppression of entry of the outside air into the supply duct 31, preferably as shown in FIG. 1, the circular orbit of the endless belt 53 may be set so that an end edge 31e at a downstream side in the circumferential direction Dc1 of the supply opening 31a of the supply duct 31 is covered over in the circumferential direction Dc1 by the endless belt 53. In this way, the outside air that enters into the supply duct 31 from a gap between the end edge 31e of the supply opening 31a and the outer circumferential face 20a of the rotating drum 20 can be suppressed, and lamination by the supply duct 31 can be stabilized.

Figure 4:
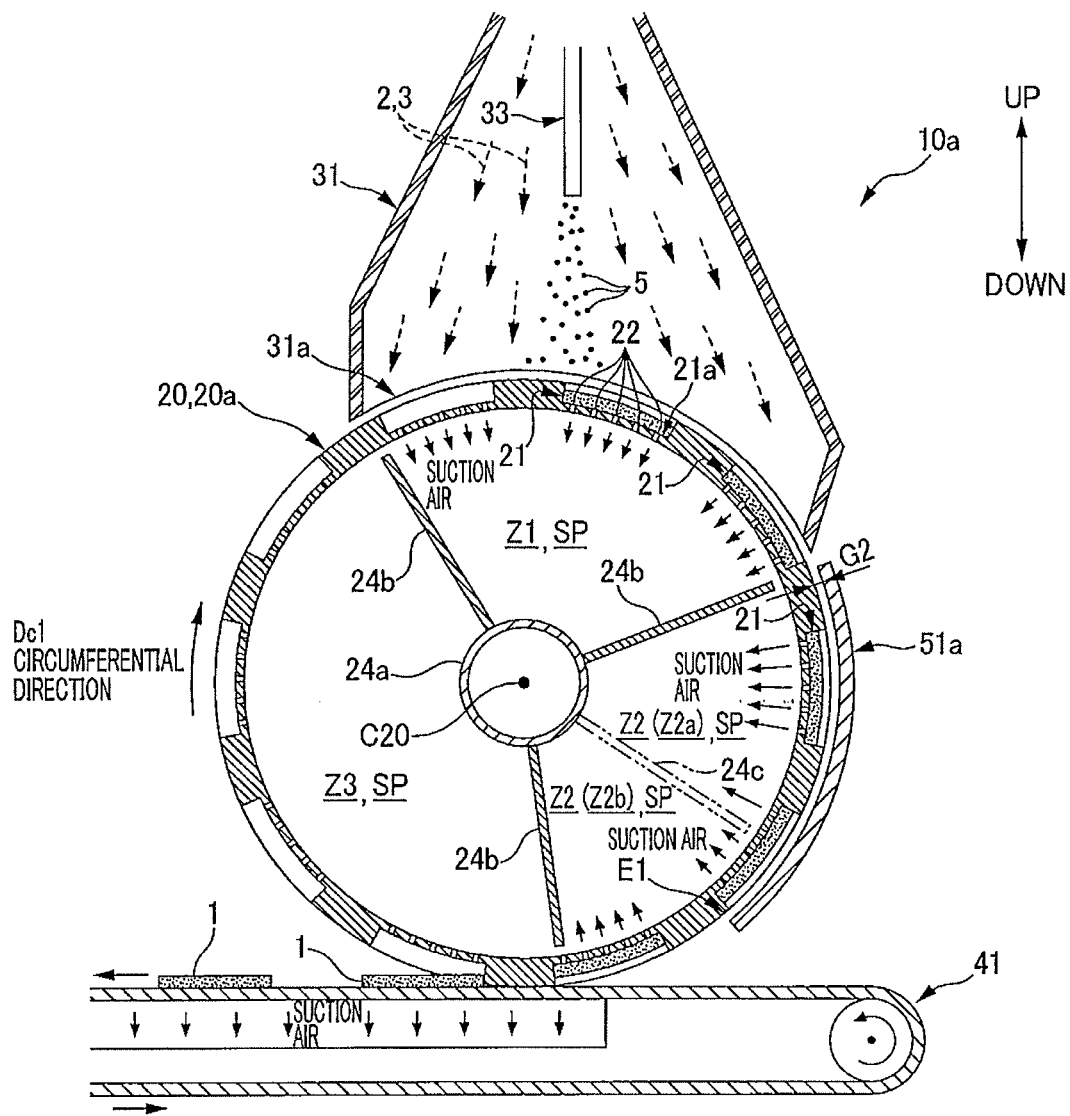
FIG. 4 is a central vertical cross sectional view of a manufacturing apparatus 10a to be used in a manufacturing method of a first modified example.

FIG. 4 is an explanatory diagram of a first modified example of the first embodiment and shows a central vertical cross sectional view of a manufacturing apparatus 10a that is used in the manufacturing method of the first modified example.

In the first embodiment, an endless belt 53 that synchronizes with the rotation of the rotating drum 20 and moves around is illustrated as a covering member, but in this first modified example, in place of the endless belt 53, in the range corresponding to the above belt setting range A1, an immovable arc shaped plate member 51a as the covering member 51a is arranged opposing the outer circumferential face 20a of the rotating drum 20. Then, with this non-air permeable arc shaped plate member 51a, inflow of the outside air into the absorbent body 1 is suppressed.

However, since this arc shaped plate member 51a is immovable, it cannot be made to closely contact the outer circumferential surface 20a of the rotating drum 20, that is, it is a structure having a space G2 in between the plate member and the outer circumferential surface 20a of the rotating drum 20 and in which the outside air can easily flow from the space G2 into the absorbent body 1. Therefore, in comparison with the endless belt 53 in the above described first embodiment, the airtightness in the mold 21 is poor, and as a result it is also inferior in ability to make the absorbent body 1 thin. Further, since it cannot move in synchronization with the mold 21 in the circumferential direction Dc1, a relative movement occurs with the absorbent body 1 that is being transported substantially integrally with the mold 21, and there is a possibility of the absorbent body 1 peeling off or a surface of the absorbent body 1 becoming rough due to twisting that occurs in a space in between the arc shaped plate member 51a and the absorbent body 1 due to this relative movement. In this regard, it is also inferior than the first embodiment. But, since a moving portion is not included, there is an advantage that its structure is simple. Another example of this immovable covering member 51a is a box member and the like that is only open on a surface that opposes the outer circumferential face 20a of the rotating drum 20. Note that, in between a peripheral edge portion of the above arc shaped plate member 51a and the outer circumferential face 20a of the rotating drum 20, a contacting seal member such as a brush may be interposed to suppress inflow of the outside air into the absorbent body 1.

Figure 5:
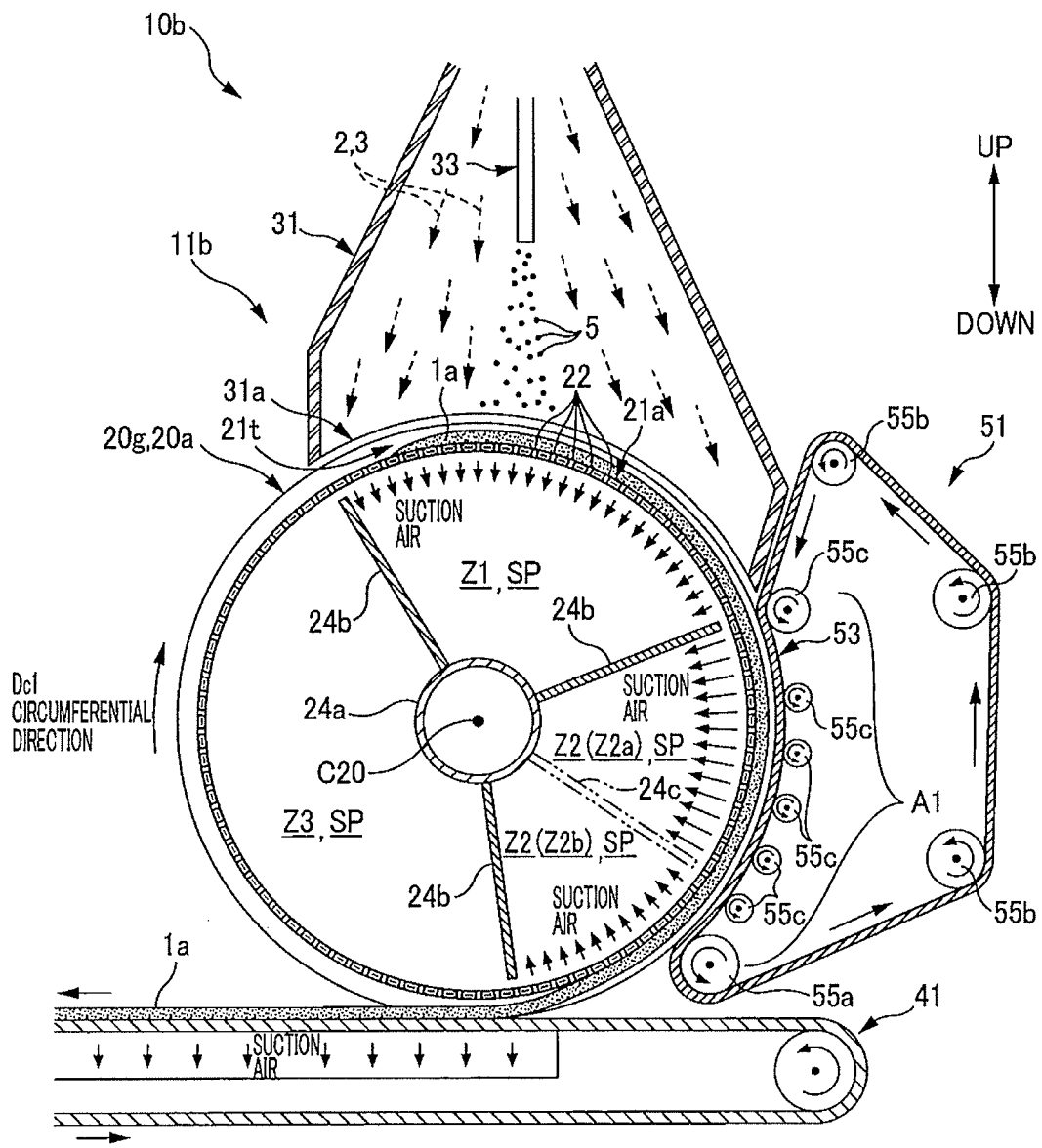
FIG. 5 is a central vertical cross sectional view of a manufacturing apparatus 10a to be used in a manufacturing method of a second modified example.
Figure 6:
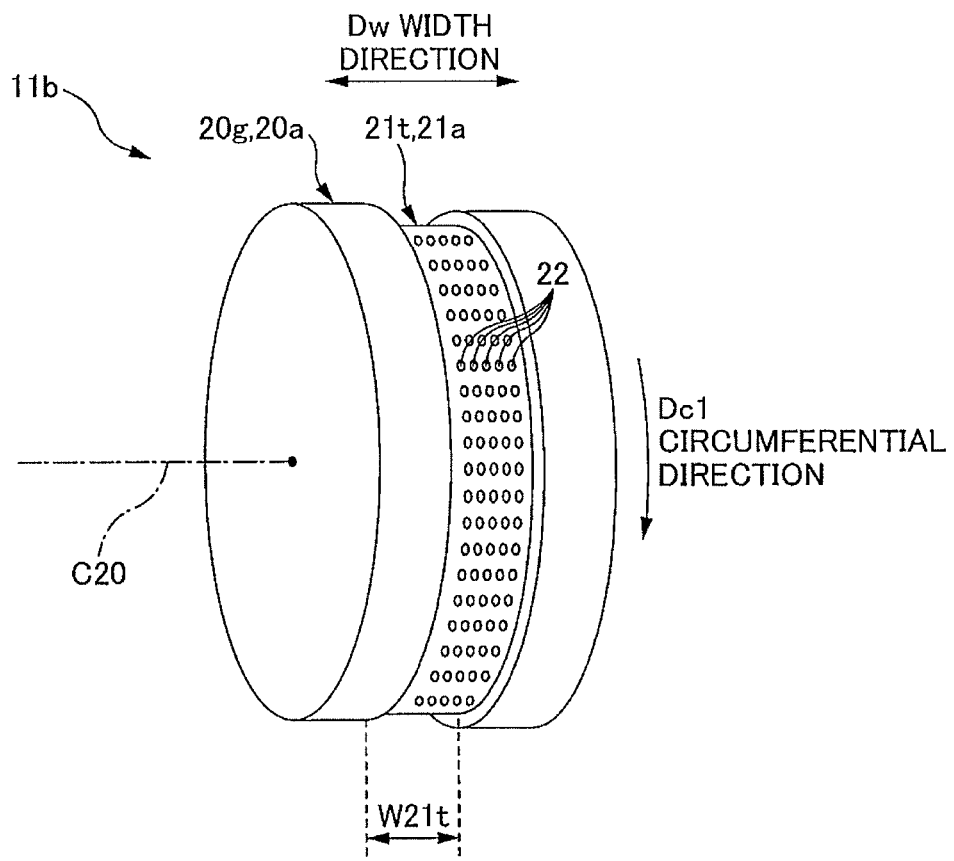
FIG. 6 is a perspective view of a rotating drum 20g of a fiber stacking apparatus 11b according to a second modified example.

FIG. 5 and FIG. 6 are explanatory views of a second modified example of the first embodiment. FIG. 5 is a central vertical cross sectional view of a manufacturing apparatus 10b used in a manufacturing method of the second modified example. FIG. 6 is a perspective view of a rotating drum 20g of a fiber stacking apparatus 11b included in the manufacturing apparatus 10b.

In the first embodiment, the absorbent body 1 is intermittently molded in the circumferential direction Dc1 of the rotating drum 20, but this second modified example differs in that a continuous body 1a of the absorbent body is molded, the continuous body 1a of the absorbent body being made with the absorbent body 1 continuously in the circumferential direction Dc1. In other words, as shown in FIG. 6, on the outer circumferential face 20a of the rotating drum 20g of the fiber stacking apparatus 11b according to this second modified example, a single groove portion 21t that continues endlessly along the circumferential direction Dc1 is formed as the mold 21t. Then, at a bottom section 21a of this groove portion 21t, as shown in FIG. 5, a plurality of suction hole 22 are provided over the entire circumference of the circumferential direction Dc1, and the pulp fiber 2 and the like are laminated in the groove portion 21t with suction air from these suction holes 22, and thus the continuous body 1a of the absorbent body is molded. Other parts are substantially the same as the above first embodiment.

Here, in the case of this second modified example, preferably, a width W53 of the endless belt 53 according to the above thinning apparatus 51 is made thinner than a width W21t of the groove portion 21t. Then, the endless belt 53 that has been sucked towards the groove portion 21t by the suction air from the suction holes 22 of the groove portion 21t can speedily enter into the groove portion 21t, and thus the continuous body 1a of the absorbent body is physically compressed in the lamination thickness direction by also a pressing force from the endless belt 53, and as a result the lamination thickness of the continuous body 1a can be made thinner.

Incidentally, in the case where a width W53 of the endless belt 53 is made thinner than a width W21t of the groove portion 21t, a portion of the continuous body 1a of the absorbent body that cannot be covered by the endless belt 53 becomes large, and a suppressing effect of the outside air inflow into the continuous body 1a of the absorbent body decreases. Therefore, the width W53 of the endless belt 53 is preferably made thin in a range of 0.8 times to 0.9 times of the width W21t of the groove portion 21t. Even if the width W53 of the endless belt 53 is slightly wider than the width W21t of the groove portion 21t, however, depending on the strength of the suction power that acts on the endless belt 53 from the suction holes 22, the endless belt 53 can go into the groove portion 21t, by both end portions of the endless belt 53 in the width direction bending and the like. In view of this, the width W53 of the endless belt 53 may be in a range of 0.9 to 1.3 times that of the width W21t of the groove portion 21t.

Further, if a rubber endless belt 53 is used, in the case of pressing the absorbent body 1 or its continuous body 1a with the endless belt 53 as described above, with a flexible elastic deformation of the endless belt 53, squashing of the superabsorbent polymers 5 that are harder than the pulp fibers 2 can be suppressed and, of the two, the pulp fiber 2 can be selectively compressed. In order to more surely enjoy this effect, a rubber endless belt 53 with a hardness of 35 to 40 A in the notation of Shore A of ISO (International Organization for Standardization) may be used.

Second Embodiment

Figure 7:
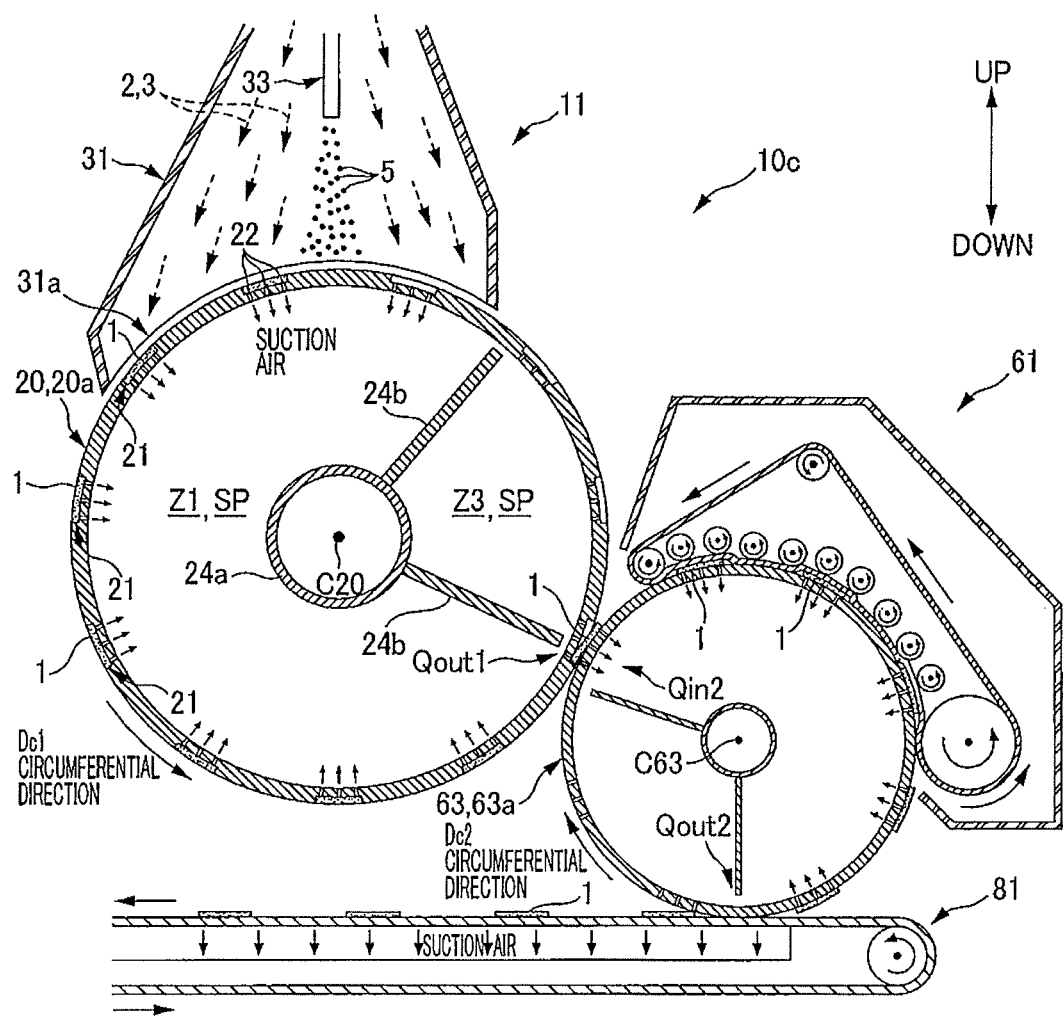
FIG. 7 is a central vertical cross sectional view of an example of a manufacturing apparatus 10c to be used in a manufacturing method in a second embodiment.
Figure 8:
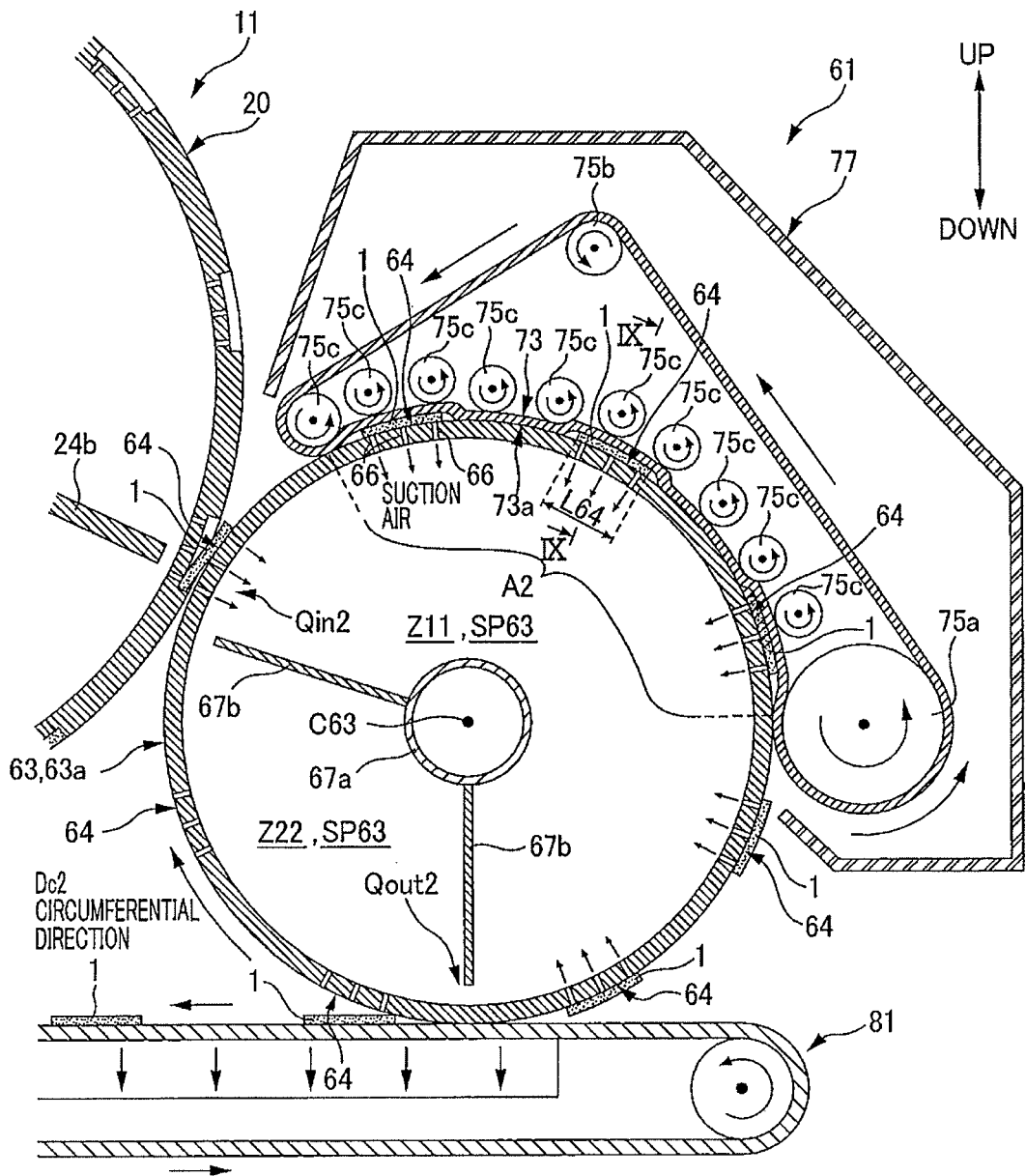
FIG. 8 is an enlarged view of a thinning apparatus 61.
Figure 9:
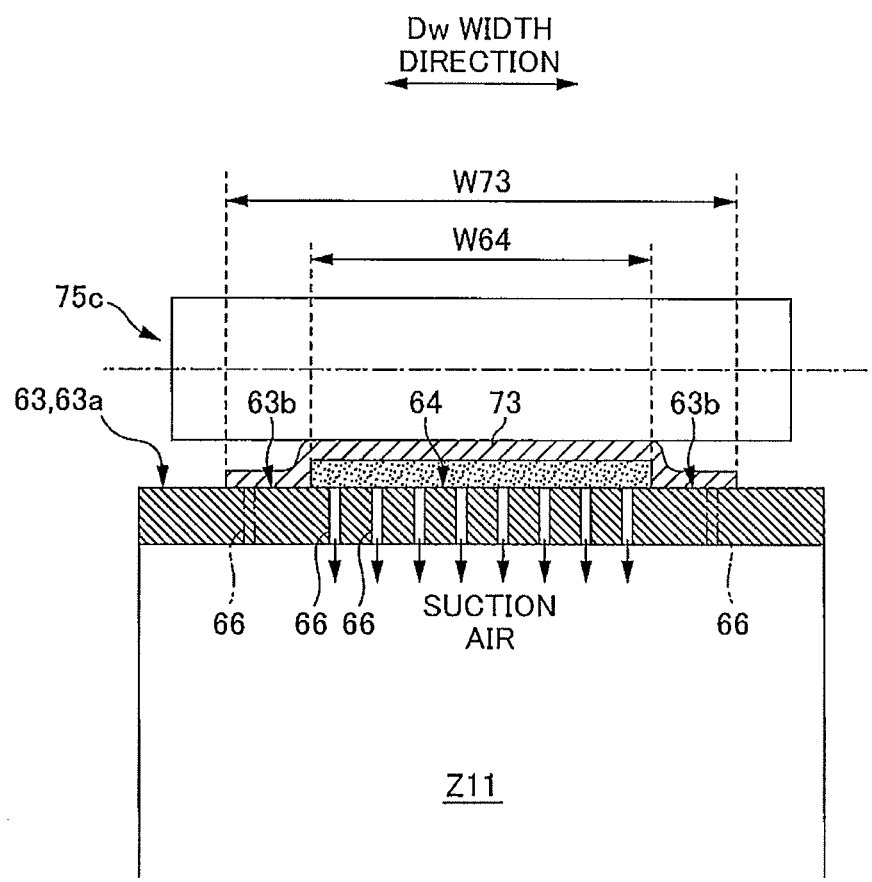
FIG. 9 is an IX-IX cross sectional view of FIG. 8.

FIG. 7 is a central vertical cross sectional view of an example of a manufacturing apparatus 10c to be used in a manufacturing method of a second embodiment. FIG. 8 is an enlarged view of a thinning apparatus 61 equipped in this manufacturing apparatus 10c. Further, FIG. 9 is an IX-IX cross sectional view of FIG. 8.

In the first embodiment, the fiber stacking apparatus 11 bears a part of the absorbent body thinning process, but in this second embodiment, the fiber stacking apparatus 11 performs merely only the absorbent body molding process, and is generally not engaged in the absorbent body thinning process. In other words, the thinning apparatus 61 according to the second embodiment receives the absorbent body 1 molded by the fiber stacking apparatus 11, and thereafter, the thinning apparatus 61 makes the lamination thickness of the absorbent body 1 thin, while transporting the absorbent body 1. In other words, the fiber stacking apparatus 11 corresponds to the "first apparatus", and the thinning apparatus 61 corresponds to the "second apparatus".

Then, according to this functionally differentiated configuration, the transferring drum 63 to be described later according to the thinning apparatus 61 can be used as an apparatus dedicated to making the lamination thickness of the absorbent body 1 thin. In other words, there is an advantage that the specification of a hole diameter of the suction holes 66, to be described later, on the outer circumferential face 63a of the transferring drum 63 and its arrangement pattern arrangement and the like can be designed as specifications specialized in making the lamination thickness thin.

The fiber stacking apparatus 11 is a generally similar structure as in the first embodiment. In other words, the fiber stacking apparatus 11 has a rotating drum 20 (corresponding to a first rotating drum) that drivingly rotates in one direction of the circumferential direction Dc1 (for example anticlockwise) with a horizontal shaft C20 as a rotational center, and is arranged with a supply duct 31 in a predetermined position in the circumferential direction Dc1 of the rotating drum 20. Further, in a position on a downstream side in the circumferential direction Dc1 of the supply duct 31, a delivery position Qout1 for handing over the absorbent body 1 that has been molded in the mold 21 on the outer circumferential face 20a of the rotating drum 20 by the supply duct 31 to the thinning apparatus 61 is set. Note that, configurations that are the same as or similar to those in the first embodiment are denoted with the same figures and explanations are omitted.

The thinning apparatus 61 also has a rotating drum 63 (hereinbelow, referred to as a transferring drum 63 (corresponding to a moving member, and a second rotating drum)). This transferring drum 63 is also a substantially cylindrical body, and drivingly rotates in one direction (for example, clockwise) in the circumferential direction Dc2 together with the rotating drum 20, with a shaft C63, that is parallel with the shaft C20 of the rotating drum 20 of the fiber stacking apparatus 11, as a rotational center. Further, this transferring drum 63 is arranged, at the above delivery position Qout1, with its outer circumferential face 63a opposing the outer circumferential face 20a of the rotating drum 20 of the fiber stacking apparatus 11. Therefore, on the transferring drum 63 side, with the delivery position Qout1 at a receiving position Qin2, the absorbent body 1 on the outer circumferential face 20a of the rotating drum 20 is received on the outer circumferential face 63a of the transferring drum 63 and held on the outer circumferential face 63a. Then, with the driving rotation of the transferring drum 63, while transporting the absorbent body 1 in the circumferential direction Dc2 along a path, along its outer circumferential face 63a, as a travel path, the absorbent body 1 is subject to a process to make its lamination thickness thin, in other words a thinning process, and thereafter, the absorbent body 1 is transported to the delivery position Qout2 in the circumferential direction Dc2, handed over to the suction conveyor 81 at the same position Qout2, and thereafter transported by the suction conveyor 81.

As shown in an enlarged view of FIG. 8, the outer circumferential face 63a of the transferring drum 63 is formed as a substantially smooth surface, and on this outer circumferential face 63a is set intermittently in a predetermined pitch in the circumferential direction Dc2 a plurality of holding surfaces 64 (corresponding to a placement surface) to hold the received absorbent body 1. Each holding surface 64, respectively, is a smooth surface with an area corresponding to a planar size of the absorbent body 1, and each holding surface 64 is arranged with a plurality of the suction holes 66 in an appropriate arrangement pattern such as a grid arrangement or a staggered arrangement. Then, each holding surface 64 has an ability to retain the absorbent body 1 using the suction air from these suction holes 66.

A suction air source of these suction holes 66 is a negative pressure space Z11 at the inner circumferential side of the transferring drum 63. More specifically, on the inner circumferential side of the transferring drum 63 is included a cylindrical division wall 67a concentrically with the transferring drum 63, and thus, on the inner circumferential side of the transferring drum 63 is defined a doughnut shaped substantially closed space SP63 (corresponding to a space). Further, this substantially closed space SP63 is zone divided in the circumferential direction Dc2 by a plurality of division walls 67b, 67b.

For example, the space is divided into two to form a first zone Z11 from a receiving position Qin2 to a delivery position Qout2, and a second zone Z22 from a delivery position Qout2 to a receiving position Qin2. Then, the first zone Z11 is maintained in a negative pressure state at an air pressure lower than the outside air pressure, and thus, by the suction air from the suction holes 66 on the holding surface 64, the absorbent body 1 received at the receiving position Qin2 is adsorbed and held on the holding surface 64. On the other hand, the second zone Z22 is maintained at an air pressure that is the same as or slightly higher than the outside air pressure, and thus, handing over of the absorbent body 1 to the suction conveyor 81 at the delivery position Qout2 can be performed smoothly.

Here, an area of the thinning process to make the absorbent body 1 thin in the circumferential direction Dc2 of the transferring drum 63 is set in a range corresponding to the first zone Z11. In other words, in a portion of this range is arranged a non-air permeable rubber endless belt 73 (corresponding to a belt member) that moves in a predetermined circular orbit. More specifically, this endless belt 73 is arranged with a portion of its circular orbit in an arc shape along the outer circumferential face 63a of the transferring drum 63. Therefore, in the range (hereinbelow, referred to as a belt setting range A2) along this arc shape, the endless belt 73 covers the absorbent body 1 from a side opposite to the holding surface 64 of the transferring drum 63 with its even outer circumferential face 73a and moves at substantially the same speed as the holding surface 64 in the circumferential direction Dc2 together with the movement of the holding surface 64.

Then, while the holding surface 64 is moving in this belt setting range A2, air in a space S in between the pulp fibers in the absorbent body 1 is sucked up by the suction air from the suction holes 66 on the holding surface 64, and at this time, the endless belt 73 effectively suppresses inflow of the outside air into the absorbent body 1. Therefore, an air pressure Pf4 of the space S in between the pulp fibers in the absorbent body 1 that is held on the holding surface 64 can be surely lower than an air pressure Pf1 of the space S in between the pulp fibers in the absorbent body 1 while laminating by the fiber stacking apparatus 11, and as a result the lamination thickness of the absorbent body 1 can be made thin.

Note that, suction of air from the suction holes 66 in this belt setting range A2 is performed based on the air pressure P11 in the above first zone Z11. The value of the air pressure P11 of the first zone Z11 is set as, for example, an air pressure value in which the air pressure Pf4 in the space S in between the pulp fibers in the absorbent body 1, that is in a state in which the absorbent body 1 on the holding surface 64 is covered by the endless belt 73, is lower than the air pressure Pf1 in the space S in between the pulp fibers in the absorbent body 1 while laminating by the fiber stacking apparatus 11.

Figure 10:
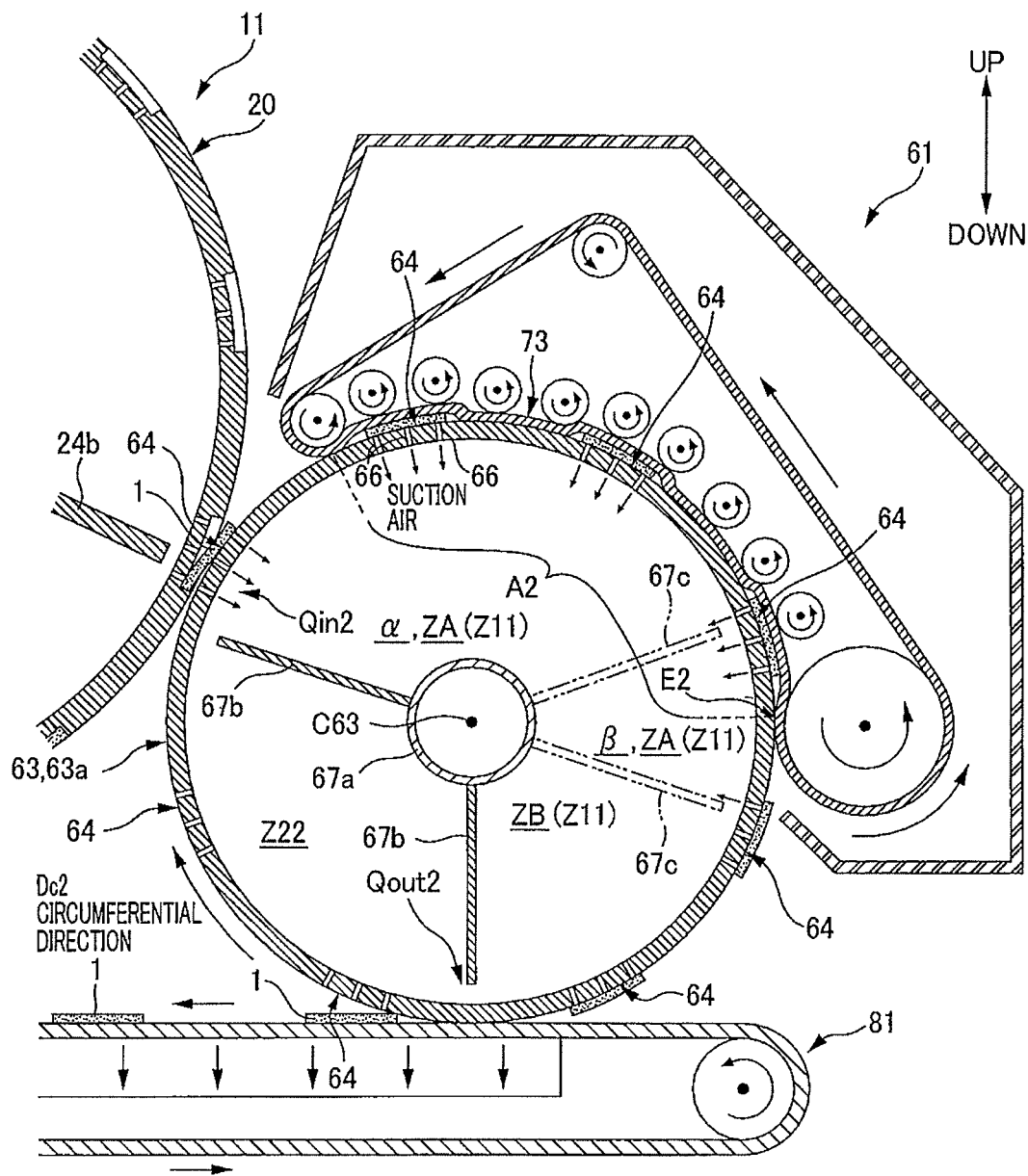
FIG. 10 is an explanatory view of an example of zone division of a first zone Z11.

Further, in some cases, the first zone Z11 may be further subdivided into a plurality of zones in the circumferential direction Dc2 by the dividing walls 67c. For example, in the example in FIG. 10, it is subdivided into three zones α, β, and ZB. That is, first, it is divided into an upstream zone ZA substantially corresponding to the above belt setting range A2 and a downstream zone ZB on a downstream side in the circumferential direction Dc2, and further, in regards to the former upstream zone ZA, it is divided into a zone α in the circumferential direction Dc2 and a zone β in the downstream side thereof. In a case where it is divided in this way, and further in the case where the air pressure Pb of the downstream zone ZB is set to be higher than the air pressure Pa of the upstream zone ZA, preferably the air pressure Pβ of the zone β may be set to an air pressure value in between the air pressure Pα in the zone β and the air pressure Pb in the downstream zone ZB. Then, the zone β corresponding to the downstream end E2 of the belt setting range A2 functions as a buffer zone for air pressure change, that is a rapid air suction pressure fluctuation that may occur in the case where the holding surface 64 moves from the low air pressure upstream zone ZA to the high air pressure downstream zone ZB can be relieved, and falling off or peeling off of the absorbent body 1 from the holding surface due to this suction air pressure fluctuation can be effectively prevented.

Further, as shown in FIG. 8 and FIG. 9, the outer circumferential face 63a of this transferring drum 63 is formed as a substantially smooth surface without a concave portion deeper than the lamination thickness t1 of the absorbent body 1 at the time it is received from the fiber stacking apparatus 11, and therefore the absorbent body 1 is held on the holding surface 64 in a state protruding from the outer circumferential face 63a. Therefore, the endless belt 73, that has been sucked towards the outer circumferential face 63a by the suction air from the suction holes 66 on the holding surface 64, can sandwich and press the absorbent body 1 with the holding surface on the outer circumferential face 63a of the transferring drum 63, and therefore the absorbent body 1 can be made thinner.

Incidentally, at the time of this sandwiching and pressing, the endless belt 73, with its flexible elastic deformation due to it being manufactured by rubber, can suppress squashing of the superabsorbent polymer 5 that is harder than the pulp fiber 2 and, of the two, selectively compress the pulp fibers 2. Note that, in order to surely enjoy these effects, a rubber endless belt 73 with a hardness of 35 to 40 A in the notation of Shore A of ISO (International Organization for Standardization) is preferably used, as described above.

Further, preferably, from the view of inflow suppression of the outside air into the absorbent body 1, preferably a width W73 of the endless belt 73 is made wider than a size W64 in the width direction Dw of the holding surface 64 as shown in FIG. 9. Then, the endless belt 73 that has been sucked towards the outer circumferential face 63a by the suction air from the suction holes 66 on the holding surface 64, adopts a closely contacting state for each portion 63b, 63b at the outer side in the width direction Dw of the holding surface 64 on the outer circumferential face 63a (corresponding to a predetermined surface) of the transferring drum 63 (corresponding to a predetermined member) as shown in FIG. 9, and therefore, inflow of the outside air from the width direction Dw is effectively prevented. Further, from a similar view, in addition to the above, preferably a length in the circumferential direction Dc2 of the belt setting range A2 is set longer than an entire length L64 in the circumferential direction Dc2 of the holding surface 64 as shown in FIG. 8. Thus, the holding surface 64 which is sucking up the air in the space S in between the pulp fibers can be covered by the endless belt 73 from all directions of its four peripheral edges (all directions of the width direction Dw and the circumferential direction Dc2), and therefore inflow of the outside air into the absorbent body 1 can be completely prevented. Note that, the suction holes 66 may be formed in respect of each portion 63b, 63b on the outer side of the outer circumferential face 63a (referred to as a chain double-dashed line), and in this way the degree of close contact of the endless belt 73 and each portion 63b, 63b on the outer side can be further increased.

By the way, in the example in FIG. 8, the circular orbit of the endless belt 73 is formed by putting the endless belt 73 around a plurality of pass-line rollers 75a, 75b, 75c arranged in predetermined positions, and at least one of these pass-line rollers 75a, 75b, 75c is configured as a driving roller 75a that has been connected to a driving source such as a motor. Therefore, by appropriate speed controlling and the like of the driving source, with the moving speed of the holding surface 64 as a target speed, when the moving speed of the endless belt 73 in the belt setting range A2 is drive controlled, as described above, the endless belt 73 and the holding surface 64 can be moved at substantially the same speed as each other.

Here, preferably, of these pass-line rollers 75a, 75b, 75c, in respect to the rollers 75c, 75c . . . that are in charge of the orbit in the belt setting range A2, in other words, the rollers 75c, 75c . . . that are in charge of an arc shaped orbit along the outer circumferential face 63a of the transferring drum 63, are guided movably in a separating direction in respect to the outer circumferential face 63a of the transferring drum 63 by appropriate guide members, and a pressing force is added in a pressing direction to the outer circumferential face 63a by an elastic member such as a spring. Then, with the pressing force, the endless belt 73 is pressed against the outer circumferential face 63a of the transferring drum 63, so that airtightness in the absorbent body 1 and a pressing force on the absorbent body 1 can be increased.

Further, as shown in FIG. 8, the entire circular orbit of this endless belt 73 may be surrounded by a non-air permeable box member 77. Here, the box member 77, in which only a surface opposing the outer circumferential face 63a of the transferring drum 63 is open, is used. Then, in this way, outside air inflow into the absorbent body 1 can be more effectively suppressed.

Further, similarly to the description of the first modified example of the first embodiment (refer to FIG. 4), in place of the endless belt 73, in a range that corresponds to the belt setting range A2, an immovable covering member, not shown, may be arranged opposing the outer circumferential face 63a of the transferring drum 63, and thus inflow of the outside air into the absorbent body 1 may be suppressed.

Further, as the rotating drum 20 of the fiber stacking apparatus 11 according to the above-described second embodiment, the rotating drum 20g according to the second modified example of the first embodiment (refer to FIG. 6) may be applied, and thus the lamination thickness in respect to the continuous body 1a of the absorbent body can be made thin.

Further, on a surface of the endless belt 73 on a side opposing the transferring drum 63, a groove portion (not shown) that can accommodate the absorbent body 1 may be provided to accommodate the absorbent body 1 in the groove portion. Then, the absorbent body 1, in which the air in the space S in between the pulp fibers is being sucked up, and the endless belt 73 can be made to be in a non-contacting state, and, as a result, squashing of the superabsorbent polymers 5 in the absorbent body 1 can be suppressed.

Other Embodiments

The embodiments of this invention have been described above, but this invention is not limited to these embodiments and modifications shown hereinbelow are possible.

In the above-described embodiments, as the endless belts 53, 73, those made of rubber are illustrated, but in some cases those made of resin or metal may be used.

In the above-described embodiments, as the covering member, the non-air permeable endless belts 53, 73, the non-air permeable arc shaped plate member 51a and the like are illustrated, but they may have slight air permeability. In other words, if it is possible to make the air pressure Pf2 in the space S in between the pulp fibers in the absorbent body 1, that is in a state in which the absorbent body 1 is covered by the covering member, lower than the air pressure Pf1 in the space S in between the pulp fibers in the absorbent body 1 while laminating, the covering member may have some air permeability. Needless to say, however, it is preferable that the belt member has no air permeability.

In the above-described first embodiment, as the covering member, the endless belt 53 with a flat outer circumferential face 53a is illustrated, however it is not limited thereto. For example, an endless belt may be used in which at least a portion that is to come into contact with the outer circumferential face 20a of the rotating drum 20 is flat, and further an endless belt with the outer circumferential face 53a that is not flat may be used. A flat face is preferable however, because each portion in the outer circumferential face 53a can closely contact with the corresponding portion, and the airtightness in the absorbent body 1 can be increased.

In the above-described second embodiment, as the covering member, the endless belt 73 with a flat outer circumferential face 73a is illustrated, but for example, an endless belt may be used in which at least a portion in the endless belt 73 that is to come into contact with the absorbent body 1, and/or a portion in the endless belt 73 that is to come into contact with the outer circumferential face 63a of transferring drum 63, is flat, and further an endless belt with the outer circumferential face 73a that is not flat may be used. A flat face, however, is preferable since each portion in the outer circumferential face 73a closely contacts the corresponding portion and can increase the airtightness in the absorbent body 1.

In the above-described embodiment, an air permeable continuous sheet such as a tissue paper or a nonwoven fabric was not wrapped around the outer circumferential face 20a of the rotating drums 20, 20g of the fiber stacking apparatuses 11, 11b, but it is not limited thereto. In other words, a continuous sheet may be wrapped around in a predetermined wraparound angle and the continuous sheet may be transported by rotation of the rotating drums 20, 20g, and when the continuous sheet passes the position on the supply duct 31, the absorbent body 1 may be laminated on the continuous sheet. Note that, in this case, in the second embodiment (FIG. 8), the continuous sheet is transported from the fiber stacking apparatus 11 to the transferring drum 63 integrally with the absorbent body 1, and at the transferring drum 63 the continuous sheet is positioned closer to the endless belt 73 side than the absorbent body 1. Therefore, by the suction air from the suction holes 66 on the outer circumferential face 63a of the transferring drum 63, when the continuous sheet is sucked toward the transferring drum 63, this continuous sheet can forcibly press the absorbent body 1, thus the absorbent body 1 can be made further thinner. Further, the continuous sheet is a tissue paper or a nonwoven fabric and the like, and has flexibility, and also functions as a buffer material that relieves the pressing force of the endless belt 73 and transfers it to the absorbent body 1, and thus squashing of the superabsorbent polymer 5 in the absorbent body 1 is suppressed.

In the above-described embodiments, the rotating drums 20, 20g were used as the fiber stacking apparatuses 11, 11b, but it is not limited thereto. For example, the mold 21 may be formed in a concave shape on the belt of the belt conveyor, the suction holes 22 may be included on the bottom section 21a of the mold 21, and the belt may be moved in a predetermined orbit, and the supply duct 31 and the like may be arranged in a predetermined position on that orbit.

Further, similarly, in the above-described second embodiment, as the thinning apparatus 61, the transferring drum 63, in other words the rotating drum 63, was used, but it is not limited thereto. For example, the holding surface 64 may be provided on the surface of the belt of the belt conveyor, and the suction holes 66 may be provided on the holding surface 64, and the belt may be moved in the predetermined orbit, then over the predetermined range on that orbit, the endless belt 73 may be arranged so as to cover the absorbent body 1 that is being held on the holding surface 64.

In the above-described embodiments, air is illustrated as an example of the gas to be discharged and supplied from the supply duct 31, but it is not limited thereto as long as it is a gas that can include, mixed therein, a liquid absorbent fiber such as the pulp fiber 2 and the superabsorbent polymer 5 and that does not chemically react or the like with the fiber and the superabsorbent polymer 5, and it may be a gas such as nitrogen.

In the above-described embodiments, the pulp fiber 2 (a pulp that has been pulverized into a fibrous state) is illustrated as the liquid absorbent fiber, but cellulose such as cotton, regenerated cellulose such as rayon and fibril rayon, semisynthetic cellulose such as acetate and triacetate, fibrous polymer, thermoplastic fiber, or a combination of the above may be used.

REFERENCE SIGNS LIST 1 absorbent body, 1a continuous body of absorbent body (absorbent body), 2 pulp fiber (liquid absorbent fiber), 3 mixed air (gas), 5 superabsorbent polymer, 10 manufacturing apparatus, 10a manufacturing apparatus, 10b manufacturing apparatus, 10c manufacturing apparatus, 11 fiber stacking apparatus (first apparatus, second apparatus), 11b fiber stacking apparatus (first apparatus, second apparatus), 20 rotating drum (moving member, first rotating drum, predetermined member), 20a outer circumferential face (predetermined surface), 20b portion, 20g rotating drum (moving member, first rotating drum, predetermined member), 21 mold, 21a bottom section (placement surface), 21t groove portion (mold), 22 suction hole, 24a cylindrical division wall, 24b division wall, 24c division wall, 31 supply duct, 31a supply opening, 31e end edge, 33 polymer inserting duct, 41 suction conveyor (mold-release mechanism), 51 thinning apparatus (second apparatus), 51a arc shaped plate member (covering member), 53 endless belt (belt member, covering member), 53a outer circumferential face, 55a pass-line roller, 55b pass-line roller, 55c pass-line roller, 61 thinning apparatus (second apparatus), 63 transferring drum (moving member, second rotating drum, predetermined member), 63a outer circumferential face (predetermined surface), 63b portion, 64 holding surface (placement surface), 66 suction hole, 67a cylindrical division wall, 67b division wall, 67c division wall, 73 endless belt (belt member, covering member), 73a outer circumferential face, 75a pass-line roller, 75b pass-line roller, 75c pass-line roller, 77 box member, 81 suction conveyor, A1 belt setting region, A2 belt setting region, E1 downstream end, E2 downstream end, G2 space, SP substantially closed space (space), Z1 first zone, Z2 second zone, Z2a zone, Z2b zone, Z3 third zone, SP63 substantially closed space (space), Z11 first zone, ZA upstream zone, ZB downstream zone, Z22 second zone, Qout1 delivery position, Qin2 receiving position, Qout2 delivery position

The invention claimed is:

1. A method of manufacturing an absorbent body for an absorbent article, the method comprising:
    molding the absorbent body, the molding including:
        preparing a drum with a mold, the mold having a suction hole at a bottom portion of the mold;
        directly supplying a gas including a liquid absorbent fiber and a superabsorbent polymer from a supply duct toward the mold;
        sucking in the gas through the suction hole at the bottom portion of the mold, and
        laminating the liquid absorbent fiber and the superabsorbent polymer on the bottom portion of the mold;
    thinning the absorbent body, the thinning including:
        after the molding and in a state in which the gas is not supplied, sucking air from the absorbent body through the suction hole at the bottom portion of the mold formed at one side of the drum that moves along a predetermined travel path, and
        suppressing an inflow of outside air into the absorbent body by the bottom portion and a belt member opposing the bottom portion and covering the absorbent body from an opposite side of the bottom portion, the belt member being in contact with an outer circumferential face of the drum and not in contact with the absorbent body,
    wherein
    a first zone is arranged on an inner side of the drum,
    a second zone is arranged on an opposite side of the mold of the drum,
    in the molding, the gas is sucked in through the suction hole at the bottom portion of the mold by maintaining the first zone in a first negative air pressure,
    in the thinning, the air is sucked in through the suction hole at the bottom portion of the mold by maintaining the second zone in a second negative air pressure, and
    the second negative air pressure is lower than the first negative air pressure.

2. The method according to claim 1, wherein
    in the molding,
        the absorbent body is molded by having the mold formed in a concave shape on the outer circumferential face of the drum, and by using the drum that continuously rotates in one direction in a circumferential direction thereof, and
        the supply duct is provided in a predetermined position in the circumferential direction and supplies the gas, with the liquid absorbent fiber and the superabsorbent polymer mixed therein, towards the outer circumferential face of the drum, and
    the molding further comprises releasing the absorbent body from the mold by a mold-release mechanism provided on a downstream side of the predetermined position in the circumferential direction.

3. A method of manufacturing an absorbent body for an absorbent article, the method comprising:
    molding the absorbent body, the molding including:
        preparing a drum with a mold, the mold having a suction hole at a bottom portion of the mold;
        directly supplying a gas including a liquid absorbent fiber and a superabsorbent polymer from a supply duct toward the mold;
        sucking in the gas through the suction hole at the bottom portion of the mold, and
        laminating the liquid absorbent fiber and the superabsorbent polymer on the bottom portion of the mold;
    thinning the absorbent body, the thinning including:
        after the molding and in a state in which the gas is not supplied, sucking air from the absorbent body through the suction hole at the bottom portion of the mold formed at one side of the drum that moves along a predetermined travel path, and
        suppressing an inflow of outside air into the absorbent body by the bottom portion and a belt member opposing the bottom portion and covering the absorbent body from an opposite side of the bottom portion, the belt member being in contact with an outer circumferential face of the drum and not in contact with the absorbent body,
    wherein
    a first zone is arranged on an inner side of the drum,
    a second zone is arranged on an opposite side of the mold of the drum,
    in the molding, the gas is sucked in through the suction hole at the bottom portion of the mold by maintaining the first zone in a first negative air pressure,
    in the thinning, the air is sucked in through the suction hole at the bottom portion of the mold by maintaining the second zone in a second negative air pressure, and
    the second negative air pressure is equal to the first negative air pressure.

4. The method according to claim 3, wherein
    in the molding,
        the absorbent body is molded by having the mold formed in a concave shape on the outer circumferential face of the drum, and by using the drum that continuously rotates in one direction in a circumferential direction thereof, and
        the supply duct is provided in a predetermined position in the circumferential direction and supplies the gas, with the liquid absorbent fiber and the superabsorbent polymer mixed therein, towards the outer circumferential face of the drum, and
    the molding further comprises releasing the absorbent body from the mold by a mold-release mechanism provided on a downstream side of the predetermined position in the circumferential direction.

* * * * *